United States Patent
Aieidan et al.

(10) Patent No.: US 12,303,254 B1
(45) Date of Patent: May 20, 2025

(54) BODY APPENDAGE POSITION PREDICTION USING ELECTROCARDIOGRAM DATA

(71) Applicant: KING SAUD UNIVERSITY, Riyadh (SA)

(72) Inventors: Rasha Mohammad Aieidan, Riyadh (SA); Arwa Mohammed Alanazi, Riyadh (SA); Ghala Ibrahim Alsougheir, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/028,392

(22) Filed: Jan. 17, 2025

(51) Int. Cl.
*A61B 5/11* (2006.01)
*A61B 5/00* (2006.01)
*A61B 5/339* (2021.01)
*A61B 5/346* (2021.01)

(52) U.S. Cl.
CPC ............ *A61B 5/1114* (2013.01); *A61B 5/339* (2021.01); *A61B 5/346* (2021.01); *A61B 5/681* (2013.01)

(58) Field of Classification Search
CPC ....... A61B 5/1114; A61B 5/346; A61B 5/339; A61B 5/681
See application file for complete search history.

(56) References Cited

U.S. PATENT DOCUMENTS

| | | |
|---|---|---|
| 11,841,920 B1 | 12/2023 | Marsden et al. |
| 11,954,260 B2 | 4/2024 | Guarnera et al. |
| 2018/0140203 A1 | 5/2018 | Wang et al. |
| 2020/0107766 A1 | 4/2020 | Liu et al. |
| 2021/0353203 A1* | 11/2021 | Burman ................. G16H 50/30 |
| 2022/0233129 A1* | 7/2022 | Liu ......................... G06N 3/044 |
| 2022/0378379 A1* | 12/2022 | Zimmerman ........ A61B 5/7275 |
| 2022/0384045 A1* | 12/2022 | Zimmerman ........ A61B 5/0006 |
| 2023/0290511 A1* | 9/2023 | Kallonen ............... G06N 3/045 |
| 2023/0388520 A1* | 11/2023 | Krummen .............. G06V 30/10 |
| 2024/0319797 A1 | 9/2024 | Korhonen et al. |
| 2024/0364528 A1* | 10/2024 | Singstad ............... H04L 9/3231 |
| 2025/0037859 A1* | 1/2025 | Tsai ........................ G06N 3/045 |

* cited by examiner

*Primary Examiner* — David E Choi
(74) *Attorney, Agent, or Firm* — Nath, Goldberg & Meyer; Joshua B. Goldberg

(57) ABSTRACT

A system and method are presented for recognizing position of a person's body appendage such as fingers using electrocardiogram data. An electrocardiogram (ECG) sensor placed on a user is in real time communication with a computing device containing a convolutional neural network (CNN) trained to receive real time ECG data and predict a position of the person's body appendage. The real time ECG sensor data is processed from digital format into an analog signal to form ECG image data. The ECG data may be converted from comma separated values (.csv) to joint photographic experts group (.jpeg) format. The output of the CNN model predicts the user appendage position from among a plurality of classified body appendage positions, such as number of fingers extended. The CNN model may include an input layer, convolutional 2D layer, batch normalization layer, rectified linear units layer, fully connected layer, softmax layer, and classification layer.

16 Claims, 5 Drawing Sheets

LAB ENVIRONMENT

RAISING ONE FINGER

RAISING TWO FINGERS

RAISING THREE FINGERS

RAISING FOUR FINGERS

RAISING FIVE FINGERS

BODY APPENDAGE POSITION PREDICTION USING ELECTROCARDIOGRAM DATA

BACKGROUND

Field

The disclosure of the present patent application relates to recognition or identification of the position of a body appendage, and particularly to the identification of the position of a body appendage based on measured ECG signals.

Description of Related Art

Detecting the position of a person's limb such as arms, hands, fingers, and/or legs using sensors has a wide range of applications across various fields such as healthcare and rehabilitation, sports performance, biomechanics, wearable technology, and fitness tracking to name a few. Currently, a person's limb position is typically recognized by sensors such as accelerometers, gyroscopes, magnetometers, and optical sensors. While each of these types of sensors has particular uses and advantages in certain applications, it may, in some situations involving rehabilitation and recovery from stroke, be beneficial to track a person's limb position using other technology.

Electrocardiography (ECG) is widely used in the medical field for detecting heart attacks, rhythm problems, blood and oxygen supply to the heart, and heart structure changes. For stroke recovery patients and athletes, the ability to use ECG data to track limb position with simultaneous heart monitoring may be desirable.

SUMMARY

The present disclosure provides a method for recognizing the position of a person's limb such as fingers, hands, arms or legs using electrocardiogram data. The method includes placing an electrocardiogram (ECG) sensor on a user such as a person, mammal, or other animal. The ECG sensor is in real time communication with a computing device such as a personal computer, smartphone or the like. The computing device is programmed with a convolutional neural network (CNN) model, wherein the CNN model is trained to receive ECG image inputs and predict the position of the person's fingers or other body appendage based on ECG image inputs. The CNN model makes a prediction of the position of the person's fingers or other body appendage from among a plurality of classified body appendage positions. The method continues by gathering real time ECG data on the computing device from the ECG sensor while an appendage of the user is in a user appendage position. The ECG data is processed into an image format to form ECG image data. The processing of the ECG data into an image format may include gathering raw ECG data as a digital signal represented as comma separated values (.csv), and converting the comma separated values to an analog signal and joint photographic experts group (.jpeg) format.

The ECG image data is input into the CNN model after which the computing device displays an output of the CNN model based on the ECG image data. The output of the CNN model predicts the user appendage position from among the plurality of classified body appendage positions. The CNN model may include an input layer, a convolutional 2D layer, a batch normalization layer, a rectified linear units layer, a fully connected layer, a softmax layer, and a classification layer.

The plurality of classified body appendage positions may include a number of fingers extended from a hand of the user, for example between one and five fingers. The plurality of classified body appendage positions may include, without limitation, thumb raised, thumb and index finger raised, thumb and index finger and middle finger raised, thumb and index finger and middle finger and ring finger raised, and thumb and index finger and middle finger and ring finger and little finger raised. In other embodiments, the plurality of classified body appendage positions may include an arm raised and an arm lowered.

The electrocardiogram sensor may be placed on a wrist of the user using, for example, a wristband or smartwatch. In other embodiments, the electrocardiogram sensor may include a standard 12-lead ECG, a Holter monitor, a chest strap, finger sensors, patches, implantable loop recorders, single-lead ECG devices, or any other ECG sensing equipment and arrangement.

Further disclosed herein is a system for recognizing body positions using an electrocardiogram sensor. The system includes an electrocardiogram (ECG) sensor configured to collect ECG data from a user wearing the ECG sensor. A computing device is configured to receive the ECG data from the ECG sensor, and process the collected ECG data into an image format. A trained convolutional neural network (CNN) model is programmed on the computing device and configured to predict a classified body position from the ECG image data. The classified body position may be a number of fingers between one and five that are extended from a hand of the user. The CNN model may include an input layer, a conventional 2D layer, a batch normalization layer, a rectified linear units (ReLU) layer, a fully connected layer, a softmax layer, and a classification layer.

The ECG sensor may be a wrist-worn ECG sensor, worn using a wristband or smartwatch. The computing device is configured to collect raw ECG data in a digital signal format and convert the raw ECG data from the digital signal format to an analog signal format as an image. The digital signal format may be a comma separated values (.csv) format used to produce an analog signal and joint photographic experts group (.jpeg) image format.

Further disclosed herein is a method of training a convolutional neural network to recognize a body appendage position of a person. The method includes placing an electrocardiogram (ECG) sensor on a person and gathering, on a computing device, a first data set from the ECG sensor while one or more appendages of the person are held stationary in a first fixed position. A second data set is gathered on the computing device from the ECG sensor while one or more appendages of the person are held stationary in a second fixed position. The first data set and second data set are processed into an image format to form a respective first image data set and second image data set. The first image data set and second image data sets are classified into respective first and second classifications. The first and second classifications indicate a respective first fixed position and second fixed position of the one or more appendages of the person. A convolutional neural network (CNN) model is trained using the first image data set and second image data set, and upon being trained the CNN model is configured to receive an ECG image data input and output a prediction of the first classification or second classification. The first classification and second classifications indicate a respective first fixed position and second fixed position of the appendage of the person.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

In the development of the present technology, a model was developed for recognition of body position, such as for example finger position, based on a conventional neural network model, to detect the position of fingers from one to five by using an electrocardiogram sensor, such as an electrocardiogram sensor found on a smartwatch.

Electrocardiography is widely used in the medical field for detecting heart attacks, rhythm problems, blood and oxygen supply to the heart, and heart structure changes with up to twelve sensors (electrodes) attached to the chest and limbs. Electrocardiography has not been used previously to detect and classify body movements. The main goal of the present work is to develop a deep-learning classification model to detect body position using an electrocardiogram sensor.

Figure 1A:
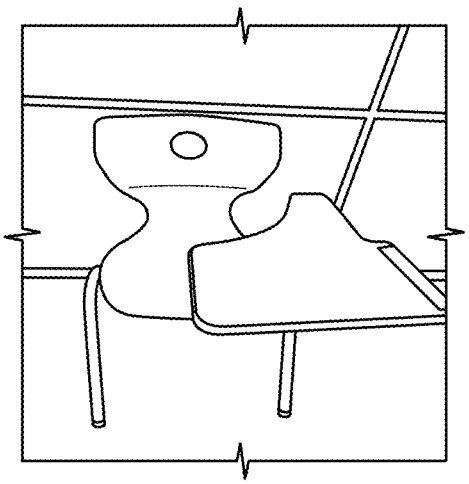
FIG. 1A is an environmental perspective view of example body positions used to develop a model for recognition of body appendage position based on electrocardiogram data.
Figure 1A:
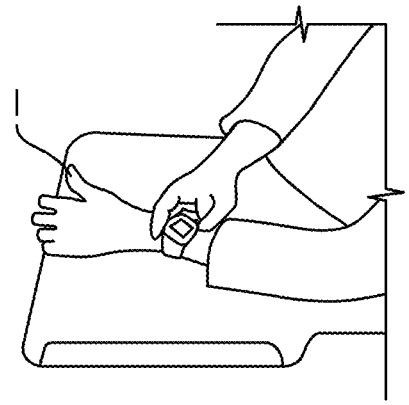
Figure 1A:
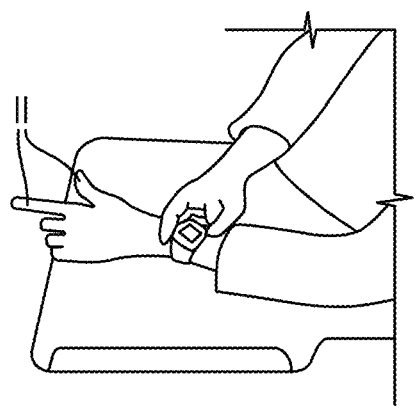
Figure 1A:
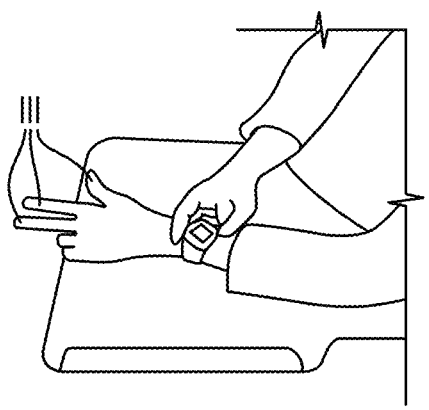
Figure 1A:
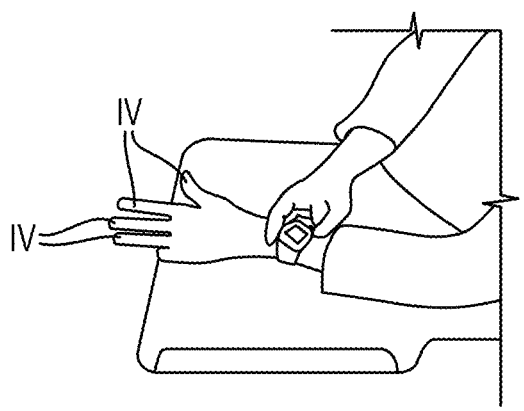
Figure 1A:
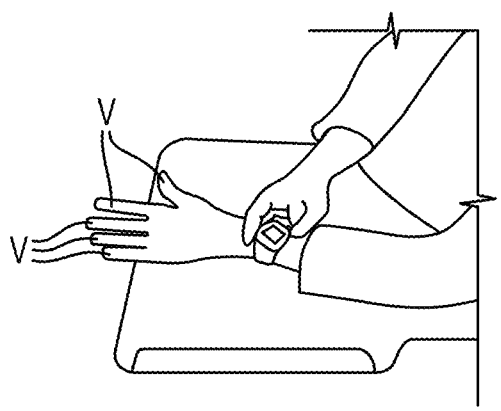

The present work used an electrocardiography sensor to recognize a body appendage position, for example the number of fingers extended on a hand, by using a smartwatch electrocardiography sensor to collect electrocardiogram signals. Participants in the study were healthy adults of age range from 21-22 with no past medical history. The environment setup was a lab in which a chair with a left-hand rest surface was used to collect data signals used for individual fingers, as shown in FIG. 1A. A plurality of body appendage positions, as shown, were assumed by participants, including a number of fingers extended from the hand of the user between one and five. The different body positions assumed equal a classified body position to be predicted by the trained deep learning model, to be explained more later. The plurality of classified body appendage positions included: thumb raised (I); thumb and index finger raised (II); thumb, index finger and middle finger raised (III); thumb, index finger, middle finger, and ring finger raised (IV); and thumb, index finger, middle finger, ring finger, and little finger raised (V).

Although the research conducted focused on recognition of finger positioning, the present methods and systems may be applied to other body positions and movements, such as detection of arm and leg positions. In other embodiments, the plurality of classified body appendage positions could include, for example, an arm raised, and an arm lowered.

Furthermore, although the electrocardiogram sensor used during the conducted research was placed on a wrist of the user, other ECG sensing arrangements could potentially be used such as, for example, a standard 12-lead ECG, a Holter monitor, a chest strap, finger sensors, patches, implantable loop recorders, single-lead ECG devices, or any other ECG sensing equipment and arrangement.

Figure 1B:
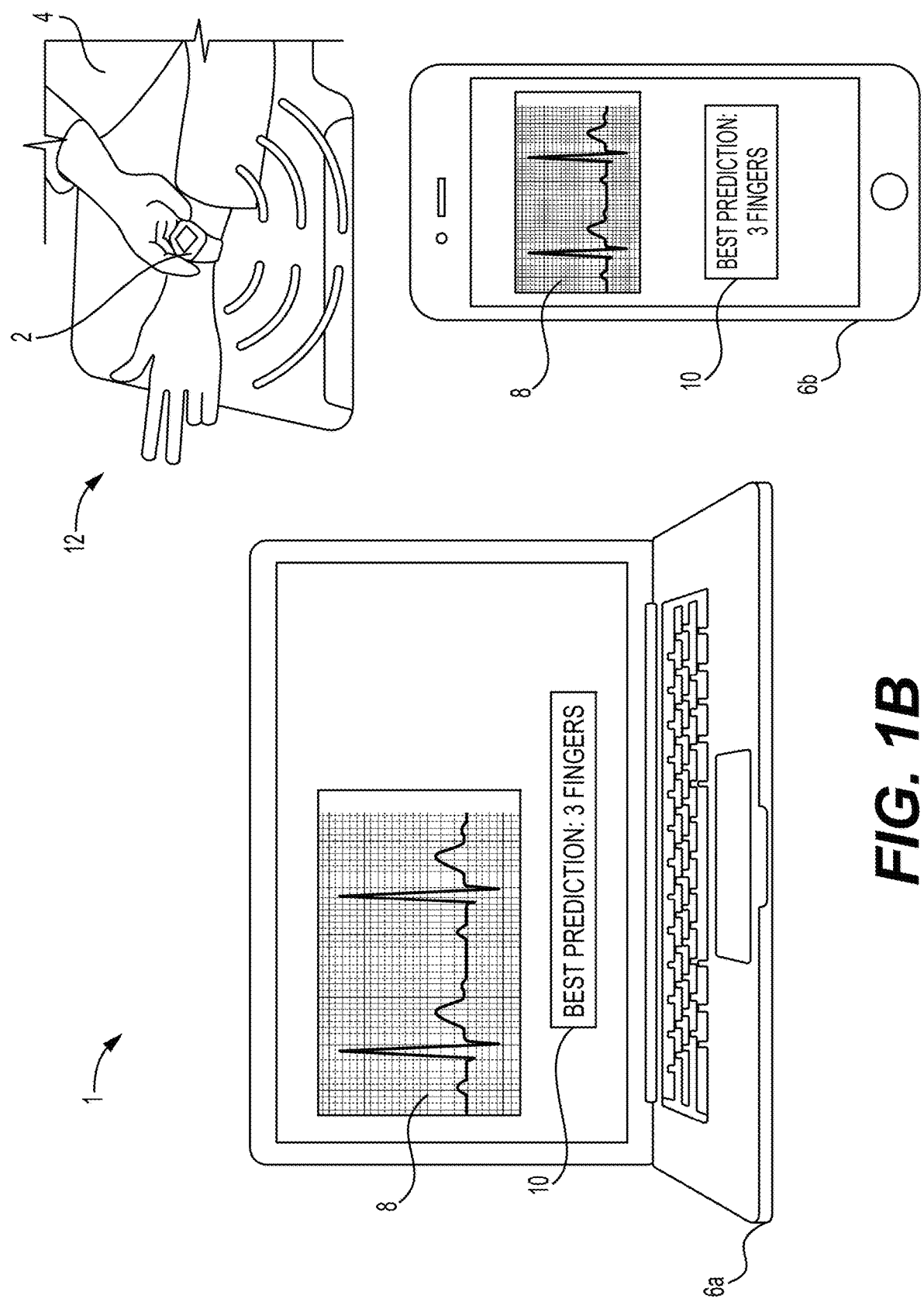
FIG. 1B is an environmental perspective view of a system for recognizing body appendage position based on electrocardiogram data.
Figure 3:
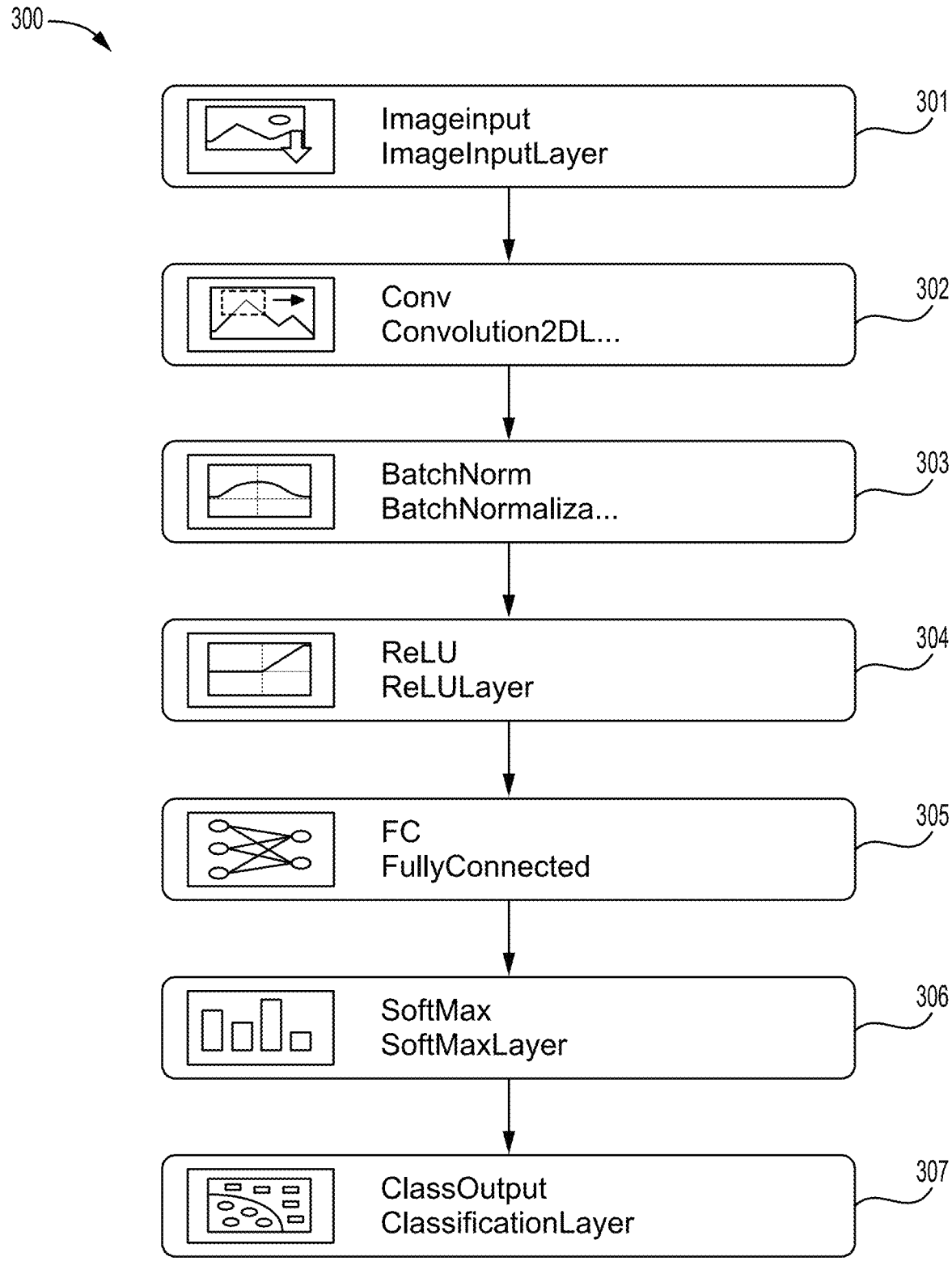
FIG. 3 is a diagram of different layers within a convolutional neural network used to determine body position based on electrocardiogram data.

Referring to FIG. 1B, a system 1 for recognizing body positions 12, still using the non-limiting example of finger positions, uses an electrocardiogram (ECG) sensor 2 configured to collect ECG data 8 from a user 4 wearing the ECG sensor 2. In the embodiment of FIG. 1B, the ECG sensor 2 is shown on a smartwatch such as that operated in the manner described in, for example, U.S. Ser. No. 10/610,157B2, which is herein incorporated by reference. A computing device such as a personal computer 6a or a smartphone 6b is configured to receive the ECG data 8 from ECG sensor 2. Although ECG sensor 2 is shown communicating wirelessly with computer 6a and smartphone 6b, it should be understood that a wired connection may also be used. Further, it should be understood that any suitable type of computing device may be used, including any suitable type of computer or the like which is capable of performing signal processing. A trained convolutional neural network (CNN) model, described later in FIG. 3, is programmed on the computing device 6 and configured to output a prediction 10 of a body position 12 of the user 4 based on the ECG data 8 transmitted from ECG sensor 2.

As is known, computing devices 6a, 6b may include any and all necessary hardware components such as one or more processors, memory components, interfaces, and displays. Examples processors may include, but are not limited to, a general purpose processor, a central processing unit (CPU), a microprocessor, a digital signal processor (DSP), a controller, a microcontroller, a state machine, a programmable logic controller, logical control circuitry or the like. The memory components may include, but are not limited to, non-transitory computer readable media: random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, or any other suitable type of non-transitory media. The interface may be any suitable type of interface allowing interaction with the computing device, and may include, but are not limited to, a combination of buttons, switches, touchscreens, keyboards or the like. A display on the computing device may include computer monitor displays, LED displays, liquid crystal displays, touchscreen displays and the like.

Figure 2A:
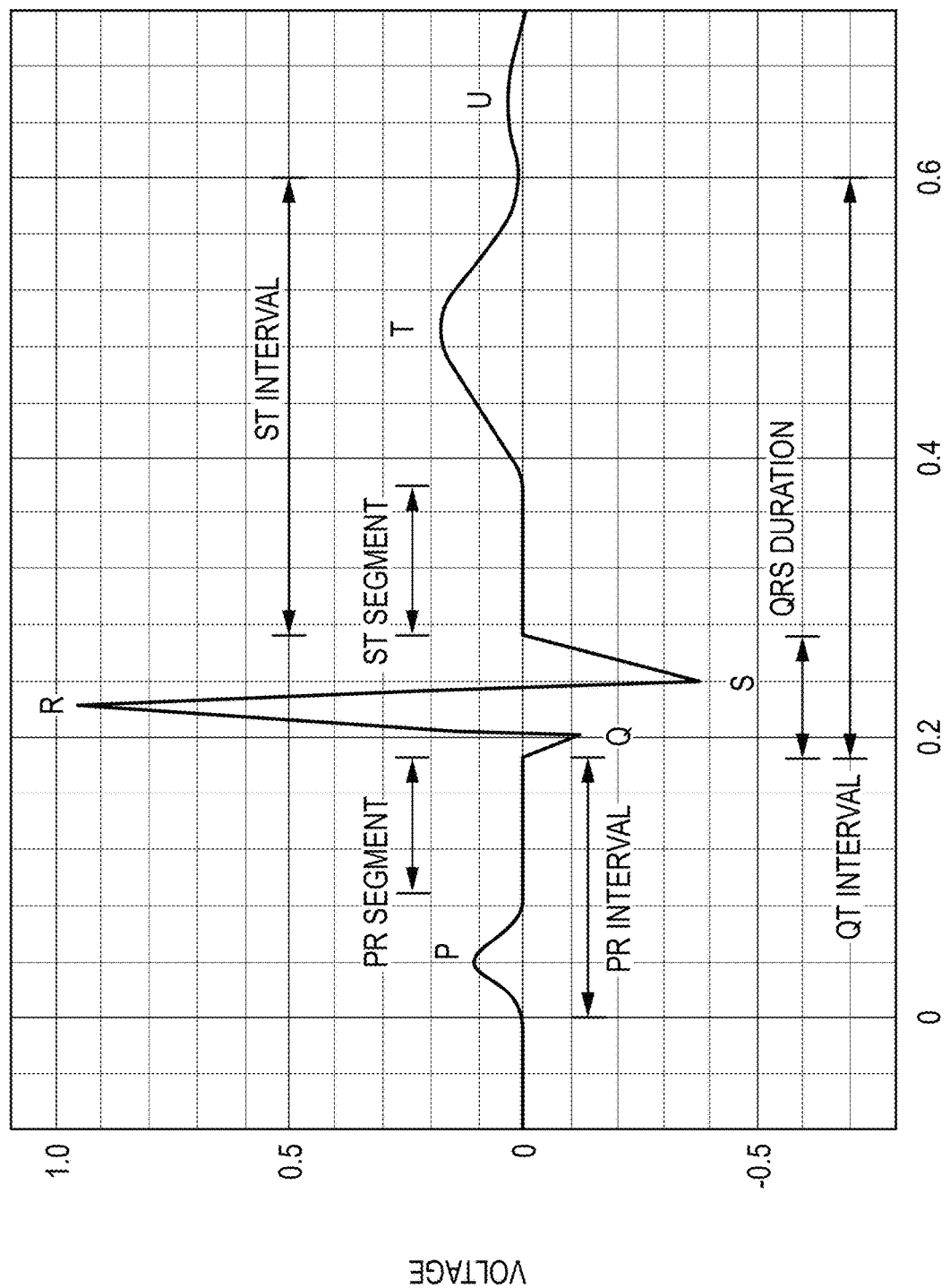
FIG. 2A illustrates a conventional electrocardiogram (ECG) waveform.

Referring to FIG. 2A, a typical ECG waveform is shown for explanation purposes. The ECG signal is a recording of electrical activity of the heart over time, providing valuable information about the heart's rhythm and function. The signal includes repeating cycles, with specific components corresponding to various phases of the cardiac system. The P wave represents atrial depolarization, or the electrical activity as the atria contract to pump blood to the ventricles. The QRS complex represents ventricular depolarization, or the electrical activity as the ventricles contract to pump blood into the lungs and body. The T wave represents ventricular repolarization, or the recovery phase of the ventricles before the next contraction. The U wave, which is sometimes present, has an exact origin which is unclear, but is thought to reflect repolarization of Purkinje fibers or papillary muscles. By interpreting the different phases of the ECG signal, various abnormalities can be predicted as is well know in the field of cardiology. However, the present teachings are believed to be the first to use ECG signals as a basis for detecting particular body appendage positions.

Figure 2B:
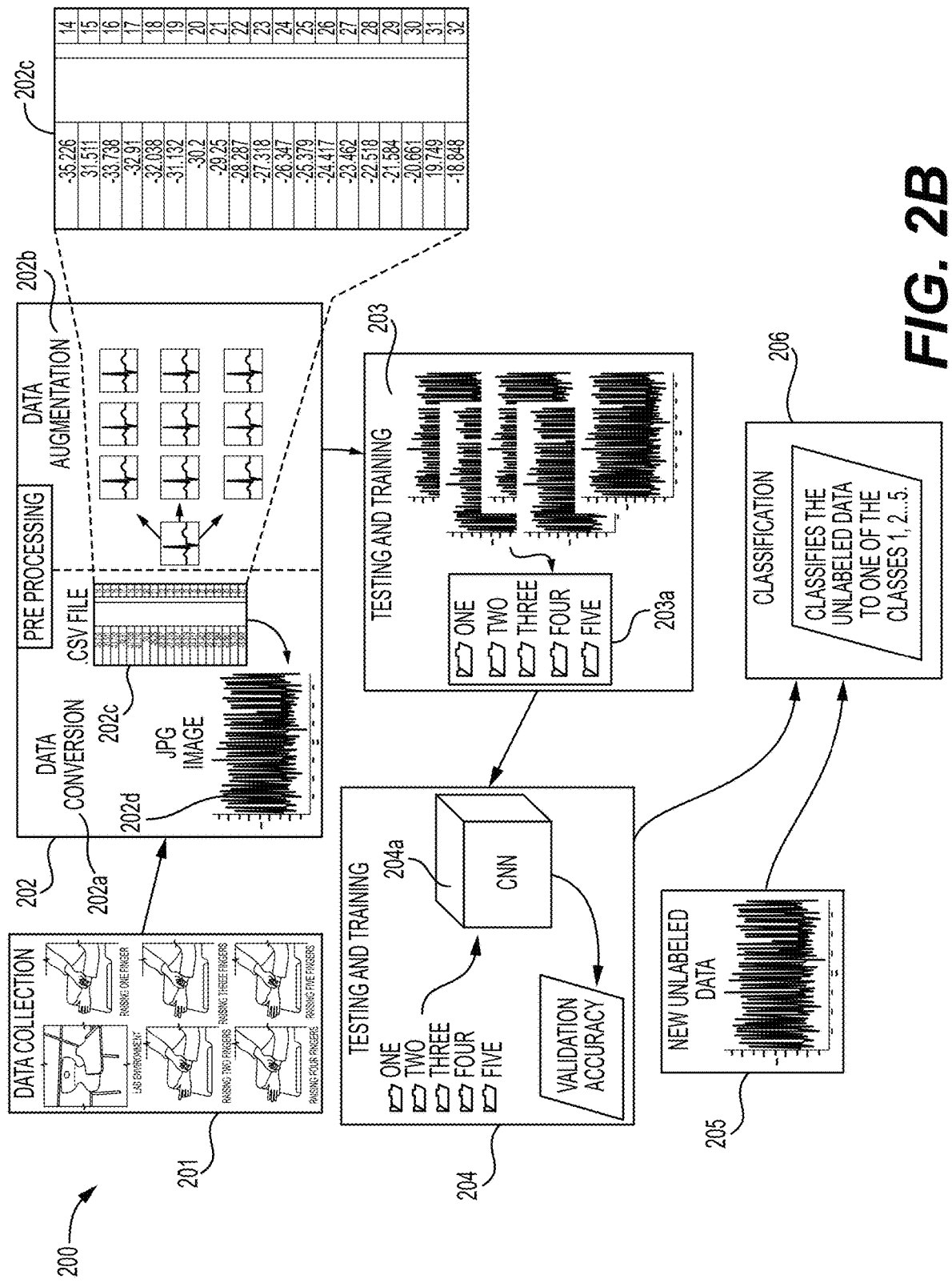
FIG. 2B is a diagram representation of system architecture stages in a system for determining body position based on electrocardiogram data.

FIG. 2B shows a diagram 200 overviewing system architecture stages 201-206 used in a system of determining body appendage position based on electrocardiogram data. Data collection stage 201 may use a lab setup, such as described in non-limiting FIGS. 1A-1B, in which a left-handed desk is used to collect ECG data on left hands of participants. A final total data set may include any number of data points such as, for example, 1000 data points, including 200 data points on each of the example positions I to V shown in FIG. 1A. Data processing stage 202 may involve two phases, data conversion 202a and data augmentation 202b. The data conversion phase 202a involves converting raw ECG sensor data into an image format such as joint photographic experts group (.JPG or .JPEG) format. After collecting raw data as a digital signal 202c in comma-separated values (.csv), the digital signal 202c is converted into an analog signal 202d in an image format (e.g. .JPG or .JPEG) showing an ECG waveform. The digital (.csv) values 202c containing digitized ECG data are typically time-series values of voltage over time. By interpreting these values, the analog ECG waveform may be reconstructed using a programming language, for example Python or MATLAB, to parse the .csv files and extract voltage-time pairs. A digital to analog converter and a microcontroller or signal generator may be used in converting the digital data into analog voltage waveform.

After the data conversion phase 202a, the second phase of data processing stage 202 may involve data augmentation 202b. If the system model is trained on a dataset that is too small, the model may result in overfitting and low accuracy. Therefore, data augmentation 202b may be used to increase the accuracy of the model. In the experimental model developed for determining finger positions, data augmentation was used to increase the original data set of 1000 to 5000. Data augmentation 202b involves artificially increasing the size and diversity of the dataset by applying transformations to the existing dataset, such as rotations, scaling, flipping, or color adjustments of the images to create new variations of the original data. Such variations help the deep learning model generalize better and become more robust to variations in the input data during real-world applications. For the data augmentation phase 202b, a deep learning framework including libraries of functions for data augmentation may be used such as imageDataAugmenter in MATLAB or TensorFlow, PyTorch, and Keras, as other examples.

After data processing stage 202, the data is organized into classes at stage 203. In the experimental model for determining finger position, data was organized into five classes 203a such as "One", "Two", "Three", "Four", and "Five" for each position I-V shown in FIG. 1A. Next, at stage 204, the data, now organized into classes, is used as an input for training and testing the convolutional neural network model 204a. The training stage 204 may use, for example, a stochastic gradient optimization algorithm. Advantageously, a stochastic gradient algorithm tends to be fast due to the reduced data processed at a given time. The data is shuffled at each epoch in the algorithm to maintain a random order of the data sample. At each training step of the algorithm a random instance of training data is received and a gradient is computed.

After training stage 204, classification may be performed at stage 206 in which new unlabeled data is received at stage 205 and input into the system. Classification 206 may be performed on the new data using, for example, a function such as MATLAB classify, in which each new image is classified into one of the classes to which the data in the training set belongs, such as classes 'One', 'Two', 'Three', 'Four' and 'Five' in the case of the experimental model for detecting finger positions. The classify function returns a class, which contains the assigned class for each ECG image of a sample.

The proposed systems rely on a convolutional neural network (CNN), which is a multi-layer feedforward neural network created by superimposing a number of invisible layers in a specific order, as shown in the example of FIG. 3. The sequential design allows CNNs to learn hierarchical attributes. The experimental model developed for determining finger positions based on ECG data used a CNN of seven layers, as shown in the example CNN model 300 FIG. 3. In a non-limiting embodiment, the CNN model 300 may include an input layer 301, a conventional 2D layer 302, a batch normalization layer 303, a rectified linear units (relu) layer 304, a fully connected (fc) layer 305, a softmax layer 306, and a classification layer 307. Input layer 301 is made of the ECG data images. The images are of a size having a height, width, and number of channels. Conventional 2D layer 302 applies convolution operations to input layer 301 using filters to extract features like edges and patterns, ultimately helping to capture spatial hierarchies in the image data. During experimental development of a prototype model, the function trainNetwork was used to compute a dot product of weights and inputs for each region and add a bias term. The set of weights applied to regions of the input layer forms a filter. The filter convolutes across the input image horizontally and vertically, repeating the same calculation for each region. In the experimental prototype finger counting model, 32 filters were used and the filter size was set to 3×3 (or, [3 3]).

Batch normalization layer 303 is used to standardize the inputs to a layer across a batch, thereby helping to stabilize the CNN model 300. During experimental development, the batch normalization process was represented by the following:

$$z = g(w, x) | z^N = [(z - m_z)/s_z] \cdot \gamma + \beta | a = f(z^N)$$

where z is the raw output or pre-activation output of a neuron in the network. The computation performed by the neuron is g(w, x) where w is the weights of the neuron and x is the input to the neuron. The batch normalization step is $z^N = [(z - m_z)/s_z] \cdot \gamma + \beta$ where $m_z$ is the mean of the neurons output, $s_z$ is the standard deviation of the neurons of the output, $s_z$ is the standard deviation of the output of the neurons, and γ and β are the learning parameters. After normalization, a neuron applies an activation function $a = f(z^N)$.

Rectified linear unit (ReLU) layer 304 introduces non-linearity into the CNN model 300, which prevents the model from behaving as a simple linear model by ensuring non-linear transformations of the input. The ReLU layer 304 is represented by $$F(x) = x, \ x \geq 0 | 0, \ x < 0$$

in which, for any input x, if x≥0, F(x)=x or, the function passes the input value x as it is. For negative values, if x<0: F(x)=0 or, the function outputs 0, effectively "zeroing out" negative values.

The fifth layer in the CNN model 300 is a fully connected (FC) layer 305. As the name suggests, every neuron in a fully connected layer connects to every neuron in the previous layer as well as every layer in the subsequent layer. The FC layer 305 combines all the features learned from the previous layers in the image to identify larger patterns.

The sixth layer in the CNN model 300 is a softmax layer 306 that applies the following function to the input:

$$P(x, 0) = (e(a_r(x, 0))) \left( \sum_{j=1}^{k} e(a_j(x, 0)) \right), \text{ where}$$

$$0 \le P(x, 0) \le 1 \text{ and } \sum_{j=1}^{k} P(x, 0) = 1$$

$$P(x, 0) = \frac{e((x, 0))}{\sum_{j=1}^{k} e(aj(x, 0))}$$

where P(x,0) is the probability assigned to class 0 given input x, $a_r(x,0)$ is the activation (or score) for class 0 produced by the model for input x. The activation or score for class j produced by the model for input x with j ranging from 1 to k (the total number of classes).

The seventh layer of the CNN Model is the classification layer 307, which takes the values from the softmax layer and uses a cross-entropy function of the 1-of-K coding scheme to assign each input to one of K mutually exclusive classes:

$$\text{Loss} = -\frac{1}{N} = \sum_{n=1}^{N} \sum_{i=1}^{k} = w_i t_{ni} \ln \ln y_{ni}$$

where N represents the number of samples, k the number of classes, w is the weight (i indicates the weight of a class), $t_{ni}$ is the nth sample if class I, $y_{ni}$ is the output of the sample n of class i. Classification layer 307 is the final layer responsible for producing predictions about the input data. It outputs the probabilities or scores for each class, which allows the model to assign the input to one of the predefined categories, or in the case of the experimental prototype model, one finger, two fingers, etc.

Experimental Trials

The following describes the trials and procedures used in development of the experimental model used for finger counting based on ECG sensor data. In a first experiment, the data collected was a total of 250, 50 data points for each class of finger positions shown in FIG. 1A, and saved as .csv files. In order to obtain an image of these signals, the digital signals of the collected raw data were converted to analog signals and saved as image files. While the experimental model used MATLAB for the digital to analog conversion and JPG images, other programs and image formats may be used within the scope of the teachings herein.

The results of the first experiment resulted in low accuracy of 61.33% for correct recognition of the finger position of participants. This was attributed to the small data set and the resulting overfitting and inaccuracy. Therefore, the data set was augmented as a solution to obtain higher accuracy and better training of the system.

A second experiment used the same setup of FIGS. 1A, 1B, but the data was augmented to a total of 1000 for each finger, or 5000 total. The number of epochs through the CNN model proved to be an important factor in the overall accuracy, as shown in Table I below.

TABLE I

Result of Second Experiment Based on Number of Epochs

| No. of Epochs | No. of Iterations | Accuracy | Elapsed Time |
|---|---|---|---|
| 10 | 200 | 24.89% | 24 min, 20 s |
| 20 | 400 | 20% | 45 min, 3 s |
| 30 | 600 | 47.82% | 3 min, 17 s |
| 40 | 800 | 90.93% | 4 min, 30 s |
| 50 | 1000 | 98.49% | 5 min, 10 s |

The results clearly indicate that ECG sensor data may be used for recognition of body position. The experimental prototype model demonstrated this by using a simple approach based on a lab environment experiment to collect ECG signals of five finger positions as digital signals in .csv form then converting those digital signals to analog signals in JPG form and using them as an input for the CNN model that successfully classified the input images with an accuracy of 98.49%.

The conclusion of the experiments conducted show that a smartwatch device may be used to obtain ECG signals which may be converted into images and input into a deep learning algorithm to analyze the ECG signal images. The main question the experimenters were looking to answer was, can ECG signals detect body positioning, such as finger positioning, by only using ECG data without additional sensors such as accelerometers, gyroscopes, etc. The experimental prototype model proved that ECG signals may be used to build a deep learning CNN model that recognizes body position (e.g. finger position) with a high accuracy of around 98%. As such, a new approach is herein provided to recognize body positioning through the use of ECG data.

It is to be understood that the systems and methods for body appendage position prediction using ECG data are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method for recognizing a user body appendage position using electrocardiogram data, comprising:
   placing an electrocardiogram (ECG) sensor on a user, wherein the ECG sensor is in real time communication with a computing device, and wherein the computing device is programmed with a convolutional neural network (CNN) model, the CNN model trained to receive ECG image inputs and predict a classified body appendage position based on the ECG image inputs from among a plurality of classified body appendage positions;
   gathering real time ECG data on the computing device from the ECG sensor while an appendage of the user is positioned in a user appendage position;
   processing the real time ECG data into an image format to form ECG image data;
   inputting the ECG image data into the CNN model;
   displaying, on the computing device, an output of the CNN model based on the ECG image data predicting the user appendage position from among the plurality of classified body appendage positions.

2. The method for recognizing a user body appendage position using electrocardiogram data as recited in claim 1, wherein the placing of the electrocardiogram sensor on the user comprises placing the electrocardiogram sensor on a wrist of the user.

3. The method for recognizing a user body appendage position using electrocardiogram data as recited in claim 1, wherein processing the ECG data into an image format comprises gathering raw ECG data as a digital signal represented as comma separated values (.csv) and converting the comma separated values to an analog signal in joint photographic experts group (.jpeg) format.

4. The method for recognizing a user body appendage position using electrocardiogram data as recited in claim 1, wherein the classified body appendage positions comprise finger positions.

5. The method for recognizing a user body appendage position using electrocardiogram data as recited in claim 1, wherein the CNN model includes an input layer, a convolutional 2D layer, a batch normalization layer, a rectified linear units layer, a fully connected layer, a softmax layer, and a classification layer.

6. The method for recognizing a user body appendage position using electrocardiogram data as recited in claim 1, wherein the classified body appendage positions include arm raised and arm lowered.

7. A system for recognizing body positions using an electrocardiogram sensor, comprising:
  an electrocardiogram (ECG) sensor configured to collect ECG data from a user wearing the ECG sensor;
  a computing device configured to receive the ECG data from the ECG sensor, the computing device configured to process the collected ECG data into an image format; and
  a trained convolutional neural network (CNN) model programmed on the computing device and configured to predict a classified body position from the ECG image data, wherein the classified body position is a number of fingers between one and five that are extended from a hand of the user.

8. The system for recognizing body positions using an electrocardiogram sensor of claim 7, wherein the ECG sensor is a wrist-worn ECG sensor.

9. The system for recognizing body positions using an electrocardiogram sensor of claim 7, wherein the computing device is configured to collect raw ECG data in a digital signal format and convert the raw ECG data from the digital signal format to an analog signal in image format.

10. The system for recognizing body positions using an electrocardiogram sensor of claim 7, wherein the digital signal format is a comma separated values (.csv) format and the image format is a joint photographic experts group (.jpeg) format.

11. The system of claim 7, wherein the CNN model comprises an input layer, a conventional 2D layer, a batch normalization layer, a rectified linear units (ReLU) layer, a fully connected layer, a softmax layer, and a classification layer.

12. A method of training a convolutional neural network to recognize a body appendage position, comprising:
  placing an electrocardiogram (ECG) sensor on a person;
  gathering on a computing device a first data set from the ECG sensor while one or more appendages of the person are held stationary in a first fixed position;
  gathering on the computing device a second data set from the ECG sensor while one or more appendages of the person are held stationary in a second fixed position;
  processing the first data set and second data set into an image format to form a first image data set and second image data sets;
  classifying the first image data set and second image data set into a respective first classification and second classification, wherein the first classification and second classification indicate the respective first fixed position and second fixed position of the one or more appendages of the person;
  training a convolutional neural network (CNN) model using the first image data set and second image data set, wherein upon being trained the CNN model is configured to receive an ECG image data input and output a prediction of the first classification or second classification.

13. The method of training a convolutional neural network to recognize a body appendage position as recited in claim 12, wherein processing the first data set and second data set into an image format comprises saving the first data set and second data set as comma separate variable (.csv) files and converting the comma separated variable files into an analog signal in joint photographic experts group (.jpeg) format.

14. The method of training a convolutional neural network to recognize a body appendage position as recited in claim 12, wherein the ECG sensor is placed on a wrist of the person.

15. The method of training a convolutional neural network to recognize a body appendage position as recited in claim 12, wherein the one or more appendages of the person held in a fixed position are a hand and fingers of the person.

16. The method of training a convolutional neural network to recognize a body appendage position as recited in claim 12, wherein the CNN model includes an input layer, a conventional 2D layer, a batch normalization layer, a rectified linear units (ReLU) layer, a fully connected layer, a softmax layer, and a classification layer.

* * * * *